United States Patent
Takeshima (10) Patent No.: US 11,797,848 B2
(45) Date of Patent: Oct. 24, 2023

(54) DATA COMPRESSION APPARATUS, DATA COMPRESSION METHOD, AND LEARNING APPARATUS

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

(*) Notice: Subject to any disclaimer, the term of this patent is extended or adjusted under 35 U.S.C. 154(b) by 0 days.

(21) Appl. No.: 17/660,897

(22) Filed: Apr. 27, 2022

(65) Prior Publication Data

US 2022/0253703 A1 Aug. 11, 2022

Related U.S. Application Data (62) Division of application No. 16/934,083, filed on Jul. 21, 2020, now Pat. No. 11,367,000.

(30) Foreign Application Priority Data

Aug. 14, 2019 (JP) .................................. 2019-148761

(51) Int. Cl.
G06K 9/00 (2022.01)
G06N 3/08 (2023.01)
G06T 11/00 (2006.01)
G06T 7/00 (2017.01)
G16H 30/40 (2018.01)
(Continued)

(52) U.S. Cl.
CPC .................. *G06N 3/08* (2013.01); *G06N 3/04* (2013.01); *G06T 7/0014* (2013.01); *G06T 11/003* (2013.01); *G16H 30/40* (2018.01); *G16H 50/20* (2018.01); *G06T 2207/10081* (2013.01);
(Continued)

(58) Field of Classification Search
CPC . G06N 3/08; G06N 3/04; G06N 3/088; G06T 7/0014; G06T 11/003; G06T 2207/10081; G06T 2207/10088; G06T 2207/20081; G06T 2207/20084; G06T 9/002; G16H 30/40; G16H 50/20; G16H 30/20
See application file for complete search history.

(56) References Cited

U.S. PATENT DOCUMENTS 8,953,862 B2 2/2015 Date et al.
2006/0269158 A1 11/2006 O'Hara
(Continued)

FOREIGN PATENT DOCUMENTS

JP 2013-052134 A 3/2013
JP 2018-120279 A 8/2018

*Primary Examiner* — Xin Jia
(74) *Attorney, Agent, or Firm* — Oblon, McClelland, Maier & Neustadt, L.L.P.

(57) ABSTRACT

According to one embodiment, a data compression apparatus includes processing circuitry. The processing circuitry generates reconstructed data by performing reconstruction processing on data. The processing circuitry generates decompressed reconstructed data by performing the reconstruction processing on decompressed data obtained by decompressing compressed data that is generated by performing compression processing on the data. The processing circuitry determines a parameter relating to a compression ratio of the data based on comparison between the reconstructed data and the decompressed reconstructed data.

1 Claim, 6 Drawing Sheets

(51) Int. Cl.
 *G06N 3/04* (2023.01)
 *G16H 50/20* (2018.01)
(52) U.S. Cl.
 CPC ............... *G06T 2207/10088* (2013.01); *G06T 2207/20081* (2013.01); *G06T 2207/20084* (2013.01)

(56) References Cited

U.S. PATENT DOCUMENTS

| | | | |
|---|---|---|---|
| 2016/0292589 A1* | 10/2016 | Taylor, Jr. | ............... G06T 9/002 |
| 2018/0211356 A1 | 7/2018 | Kurahashi | |
| 2018/0277068 A1 | 9/2018 | Diederich et al. | |
| 2021/0082444 A1* | 3/2021 | Fejgin | ................... G06N 3/045 |

\* cited by examiner

DATA COMPRESSION APPARATUS, DATA COMPRESSION METHOD, AND LEARNING APPARATUS

CROSS-REFERENCE TO RELATED APPLICATIONS

This application is a division of U.S. application Ser. No. 16/934,083, filed Jul. 21, 2020, which is based upon and claims the benefit of priority from the prior Japanese Patent Application No. 2019-148761, filed Aug. 14, 2019, the entire contents of which are incorporated herein by reference.

FIELD

Embodiments described herein relate generally to a data compression apparatus, a data compression method and a learning apparatus.

BACKGROUND

In recent years, along with increases in performance of medical image diagnosis equipment, the amount of data to be treated, such as data acquired by a medical image diagnosis apparatus (e.g., raw data), has been increasing. To efficiently store and transfer such data, it is necessary to compress the data. There are two main types of compression: lossless compression (reversible compression) processing and lossy compression (irreversible compression) processing. From the point of view of data compression efficiency, the lossy compression is preferable. Therefore, in the medical field, there is a demand for application of the lossy compression technique such as JPEG (Joint Photographic Experts Group) or MPEG (Moving Picture Experts Group).

However, if the lossy compression processing is applied to raw data, the extent to which distortion caused by the lossy compression may occur in a reconstructed image generated by the subsequent reconstruction processing is not taken into account. Thus, since the relationship between the raw data and the reconstructed data based on the raw data is not taken into account, it is unclear what influence is exerted on the reconstructed image by the distortion that occurs when the raw data is processed using lossy compression. Accordingly, there is a case in which the compression ratio of the raw data must be lowered even if it could be higher.

DETAILED DESCRIPTION

In general, according to one embodiment, a data compression apparatus includes processing circuitry. The processing circuitry generates reconstructed data by performing reconstruction processing on data. The processing circuitry generates decompressed reconstructed data by performing the reconstruction processing on decompressed data obtained by decompressing compressed data that is generated by performing compression processing on the data. The processing circuitry determines a parameter relating to a compression ratio of the data based on comparison between the reconstructed data and the decompressed reconstructed data.

In the following descriptions, a data compression apparatus, a data compression method, and a learning apparatus according to the embodiments will be described with reference to the drawings. In the embodiments described below, elements assigned with the same reference symbols are assumed to perform the same operations, and redundant descriptions thereof will be omitted as appropriate. Hereinafter, an embodiment will be described with reference to the accompanying drawings.

First Embodiment

An example of a data compression apparatus according to the first embodiment will be explained with reference to the block diagram of FIG. 1. The data compression apparatus 1 according to the first embodiment includes processing circuitry 2, an input interface 4, a communication interface 6, and a memory 8.

The processing circuitry 2 includes an acquisition function 21, a compression function 22, a decompression function 23, a reconstruction function 24, and a determination function 25. The processing circuitry 2 includes an unillustrated processor as a hardware resource.

The acquisition function 21 acquires data to be compressed from an external apparatus. The present embodiment is described on the assumption that data to be compressed is so-called raw data, which is collected by an external medical image processing apparatus. Examples of raw data may be detected data or sinogram data in the case of a computed tomography (CT) apparatus, and may be k-space data in the case of a magnetic resonance imaging (MRI) apparatus.

The compression function 22 compresses raw data at a designated compression ratio and generates compressed data. The compression ratio in this embodiment indicates to what extent the original data size is compressed. In other words, the original data size is reduced by the compression to the compressed data. The higher the compression ratio, the smaller the data size of the compressed data. As a method for compressing raw data, in this embodiment, lossy compression using orthogonal transformation, quantization, or entropy coding is assumed. However, any compression method for executing lossy compression processing may be adopted. The compression ratio may be designated by, for example, using a default setting value, or designated by a user, or designated by the determination function 25 as will be described later.

The decompression function 23 decompresses the compressed data and generates decompressed data.

The reconstruction function 24 reconstructs the raw data and generates reconstructed data. Furthermore, the reconstruction function 24 reconstructs the decompressed data, and generates decompressed reconstructed data. If the raw data is data acquired by spectral CT, data on material discrimination may be used as reconstructed data or decompressed reconstructed data. Alternatively, a function image, such as a T1 map or an apparent diffusion coefficient (ADC) map, may be used as reconstructed data or decompressed reconstructed data.

The determination function 25 determines a parameter relating to the compression ratio of data based on comparison between the reconstructed data and the decompressed reconstructed data.

The input interface 4 includes circuitry that receives various types of instructions and information input from the user. The input interface 4 includes circuitry relating to, for example, a pointing device such as a mouse, or an input device such as a keyboard. The circuitry included in the input interface 4 is not limited to circuitry relating to a physical operational component, such as a mouse or a keyboard. For example, the input interface 4 may include electrical signal processing circuitry which receives an electrical signal corresponding to an input operation from an external input device provided separately from the data compression apparatus 1 and outputs the received electrical signal to various circuitry in the data compression apparatus 1.

The communication interface 6 executes data exchange with an external apparatus by wired or wireless connections.

The memory 8 stores the raw data, the reconstructed data, the decompressed reconstructed data, etc. The memory 8 is a semiconductor memory element, such as a random access memory (RAM) and a flash memory, a hard disk drive (HDD), a solid state drive (SSD), an optical disk, etc. The memory 8 may be, for example, a drive that reads and writes various kinds of information on a portable storage medium such as a CD-ROM drive, a DVD drive, or a flash memory, etc.

The compression processing by the compression function 22 and the decompression processing by the decompression function 23 of the present embodiment may be executed by an external apparatus. In this case, the data compression apparatus 1 may transmit raw data and parameter information relating to a compression ratio to the external apparatus, the external apparatus may compress the raw data in accordance with the parameter information and decompress the compressed data, and the data compression apparatus 1 may receive the decompressed data from the external apparatus. Furthermore, the data compression apparatus 1 may transmit the parameter information relating to the compression ratio finally determined to the external apparatus, and may receive the compressed data compressed at the determined compression ratio.

Various functions performed by the processing circuitry 2 are stored in the memory 8 in the form of a program executable by a computer. The processing circuitry 2 is a processor that reads programs corresponding to the various functions from the memory 8 and executes them to realize functions corresponding to the programs. In other words, the processing circuitry 2 that has read the programs has, for example, the functions shown in the processing circuitry 2 depicted in FIG. 1.

Figure 1:
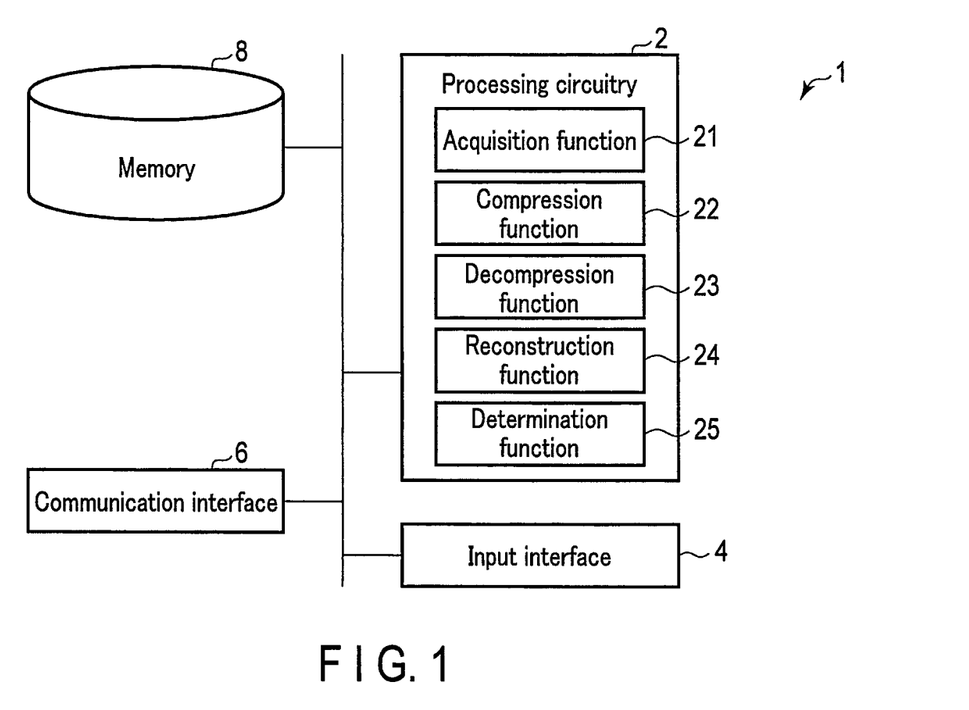
FIG. 1 is a block diagram showing a data compression apparatus according to a first embodiment.

FIG. 1 illustrates the case where the various functions are realized in single processing circuitry 2; however, the processing circuitry 2 may be constituted by a combination of a plurality of independent processors, and the functions may be realized by the processors executing the programs. In other words, the above-described functions may be configured as programs, and executed by single processing circuitry; alternatively, the functions may be implemented in independent program-execution circuitry specific to the respective functions.

Next, an operation example of the data compression apparatus 1 according to the first embodiment will be described with reference to the flowchart of FIG. 2.

In step S201, the processing circuitry 2 acquires raw data by executing the acquisition function 21.

In step S202, the processing circuitry 2 executes reconstruction processing on the raw data and generates reconstructed data by executing the reconstruction function 24. The reconstruction processing here may be provisional reconstruction processing. The provisional reconstruction processing involves simple reconstruction with a lower processing load as compared to image reconstruction processing for use in actual image diagnosis (hereinafter referred to as the main reconstruction processing). For example, if an iterative reconstruction method is used as the main reconstruction processing, a filtered back projection (FBP) method or a convolution back projection (CBP) method, which executes processing with a lighter processing load than the iterative reconstruction method, may be used as the provisional reconstruction processing. The main reconstruction processing may be executed instead of the provisional reconstruction processing.

In step S203, by executing the compression function 22, the processing circuitry 2 compresses the raw data at the designated compression ratio, and generates the compressed data.

In the compression processing, specifically, the raw data is divided into blocks of a predetermined size, and a discrete cosine transform (DCT) is executed in units of blocks. As a result, a group of pixels that are arranged two dimensionally (namely, an image) is decomposed into frequency components represented by a base image. The size of a base component relating to each base image is also referred to as a DCT coefficient. Subsequently, the DCT coefficient is quantized with reference to a quantization table representing a quantization level. By increasing the quantization level, a larger amount of information can be reduced. Subsequently, entropy coding processing or arithmetic coding processing is executed on the quantized value, thereby generating compressed data. For example, Huffman coding may be adopted as the entropy coding.

As the orthogonal transformation, a discrete wavelet transformation or any other orthogonal transformation may be adopted. Alternatively, 5/3 wavelet transformation or 9/7 wavelet transformation may be adopted, in which compression and decompression are biorthogonal. Since general processing can be adopted as the compression processing, detailed description of the processing is omitted.

In step S204, by executing the decompression function 23, the processing circuitry 2 decompresses the compressed data and generates the decompressed data. As the data decompression processing, for example, if the compression processing as in step S203 has been executed, the variable-length coded data is decoded and inverse quantized, and an inverse DCT transformation is executed, so that the decompressed data is generated. Since general processing can be adopted as the data decompression processing by the decompression function 23, detailed description of the processing is omitted.

In step S205, by executing the reconstruction function 24, the processing circuitry 2 executes the reconstruction processing on the decompressed data and generates the decompressed reconstructed data. The reconstruction processing in step S205 is the same as the reconstruction processing in step S202. That is, the provisional reconstruction processing is executed here.

In step S206, by executing the determination function 25, the processing circuitry 2 calculates an error between the reconstructed data calculated in step S202 and the decompressed reconstructed data calculated in step S205. The error may be a difference between pixels at the same spatial coordinates of an image based on the reconstructed data and an image based on the decompressed reconstructed data, or a least-squares error therebetween. Alternatively, an L1 error (an estimated value based on L1 regularization) or an L2 error (an estimated value based on L2 regularization) may be used.

In step S207, by executing the determination function 25, the processing circuitry 2 stores the error calculated in step S206 and the compression ratio of the compression processing in step S203 in association with each other. For example, a table in which errors and compression ratios are associated with each other may be stored in the memory 8. Compression ratios may be stored in association with parameters for compression processing at the corresponding compression ratios. The relationship between the errors and the compression ratios is not necessarily managed by the table, and may be stored in any form that can store the correspondence between the errors and the compression ratios.

In step S208, by executing the determination function 25, the processing circuitry 2 determines whether or not generation of decompressed reconstructed data is executed for one piece of raw data a predetermined number of times. In other words, in step S208, it is determined whether or not the compression processing has been executed at different compression ratios a predetermined number of times. This is because the relationship between raw data and a deterioration quantity of a reconstructed image due to compression of the raw data is considered to vary depending on the type of the medical image diagnosis apparatus and the position of an imaging target. The method used for determination may be as follows: for example, a counter with the initial value 0 is prepared in advance, and each time the processing of step S207 is completed, the counter is incremented by one; and if the counter reaches a predetermined number, it is determined that the generation of decompressed reconstructed data has been executed the predetermined number of times. If the generation of decompressed reconstructed data has executed the predetermined number of times (step S208, YES), the flow proceeds to step S210. If not (step S208, NO), the flow proceeds to step S209.

In step S209, by executing the compression function 22, the processing circuitry 2 changes the compression ratio in the compression processing in step S203. The compression ratio may be changed as follows: for example, a plurality of quantization tables with different compression ratios are prepared in advance, and quantization is executed using an unapplied quantization table that is different from the quantization table applied in the processing in the steps described above, so that the compression ratio can be changed.

The compression ratio is not necessarily changed by changing the quantization table, but can be changed by adopting any other method that can change the compression ratio.

In step S210, by executing the determination function 25, the processing circuitry 2 acquires, at the different compression ratios, sets of the relationships between the errors and the compression ratios executed the predetermined number of times, namely, the relationships between the compression ratios of raw data and the image qualities of the reconstructed images, and determines a parameter relating to an optimum compression ratio from the plurality of sets of the compression ratios and the errors of the reconstructed images. The compression ratio may be determined by, for example, selecting a parameter relating to the compression ratio by which the error between the reconstructed data and the decompressed reconstructed data is equal to or smaller than a first threshold value, and the compression ratio of the compression processing is equal to or greater than a second threshold value. Specifically, if the compression ratio is prioritized, the optimum compression ratio to be determined may be the highest compression ratio of the compression ratios, by which the error between the reconstructed data and the decompressed reconstructed data is equal to or smaller than the threshold and the compression ratio is equal to or greater than the threshold. Accordingly, the data can be compressed at a high compression efficiency, while the image quality is maintained to a certain degree even in the reconstructed image. If the image quality of the reconstructed image is prioritized, since the lower the compression ratio, the higher the image quality, the optimum compression ratio to be determined may be the lowest compression ratio of the compression ratios, by which the error between the reconstructed data and the decompressed reconstructed data is equal to or smaller than the threshold, and the compression ratio is equal to or greater than the threshold (in other words, the compression ratio corresponding to the smallest error between the reconstructed data and the decompressed reconstructed data).

Although the processing circuitry 2 may determine the optimum compression ratio by executing the determination function 25, a priority standard as to whether the compression ratio or the image quality of the reconstructed image should be prioritized may be determined as needed. For example, a display or the like may display items "compression ratio prioritized" or "image quality prioritized" via the communication interface 6, so that the user can select either of the items, and the optimum compression ratio may be determined in accordance with the priority standard selected by the user.

Alternatively, the optimum compression ratio may be determined, based on a trained model using the relationship between the error and the compression ratio as an input and the optimum compression ratio as correct answer data, by applying the trained model to the relationship between the error and the compression ratio.

In step S211, by executing the compression function 22, the processing circuitry 2 compresses the raw data at the compression ratio determined in step S210. This concludes the operation of the data compression apparatus 1.

Figure 2:
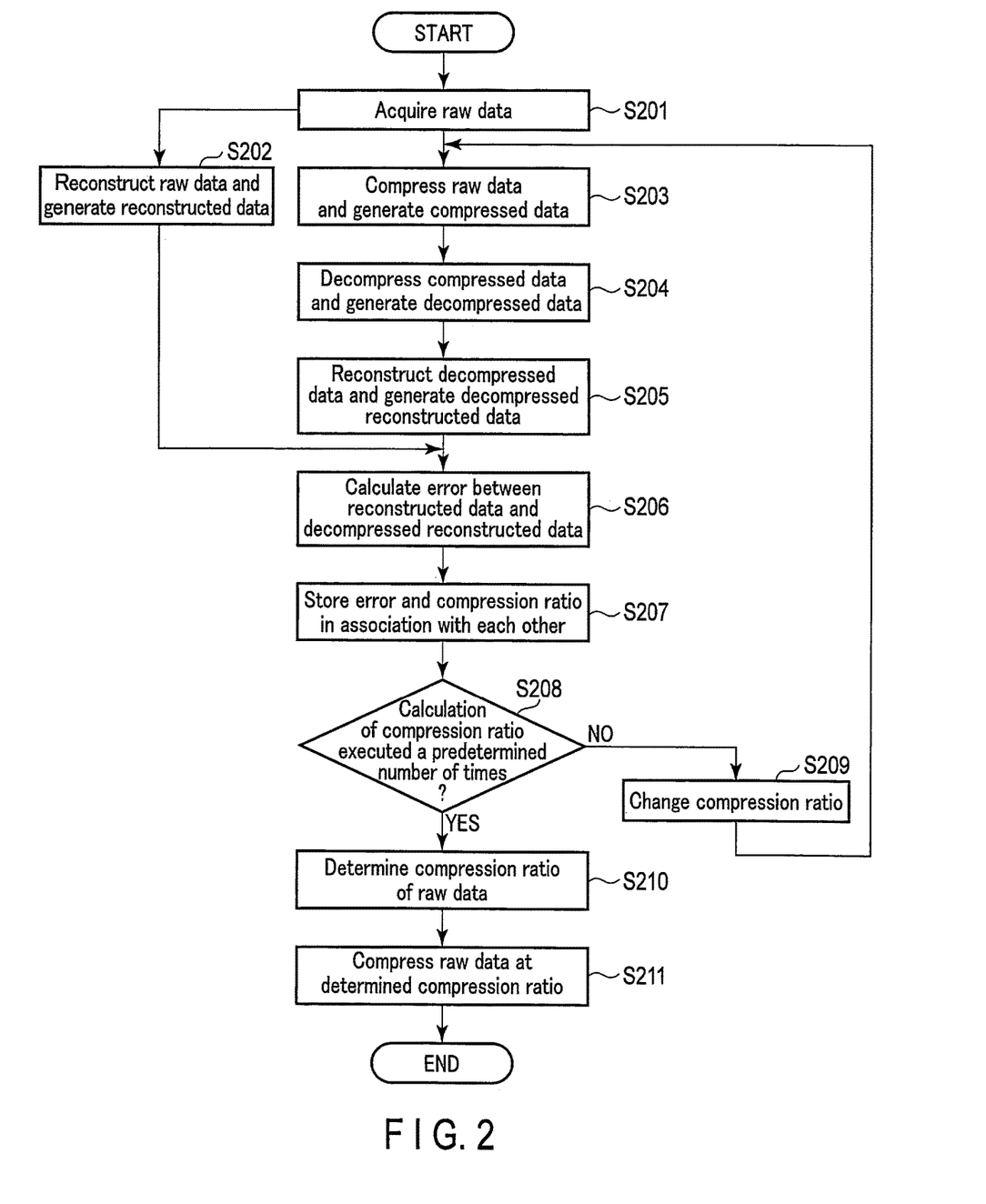
FIG. 2 is a flowchart showing an example of an operation of the data compression apparatus according to the first embodiment.

In the example shown in FIG. 2, it is assumed that the compression ratio is changed by changing the quantization table; however, the method of compression processing itself may be changed to change the compression ratio.

Next, a conceptual diagram showing the relationship between the error of a reconstructed image and the compression ratio of raw data will be explained with reference to FIG. 3.

Figure 3:
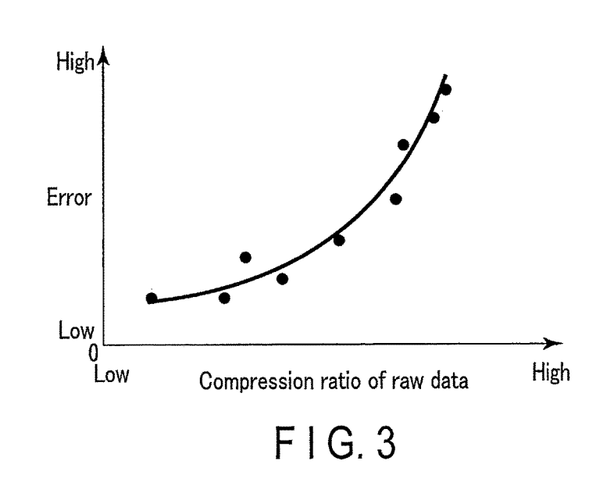
FIG. 3 is a graph showing the relationship between an error and a compression ratio of raw data concerning a reconstructed image.

In the graph of FIG. 3, the horizontal axis represents the compression ratio of raw data, and the vertical axis represents the error between reconstructed data and decompressed reconstructed data. In the graph, an approximate curve can be generated by plotting the relationship between the error and the compression ratio acquired in step S207, and executing fitting processing for the plot.

It is assumed that the processing circuitry 2 automatically determines the optimum compression ratio by the determination method in step S210 by executing the determination function 25; however, the processing circuitry 2 may create the graph shown in FIG. 3 by executing the determination function 25, and provide it to the user.

As shown in FIG. 3, the higher the compression ratio, the greater the error. Therefore, the user may select a compression ratio at which the deterioration quantity of the reconstructed image is permissible, while viewing the graph. For example, the user may select the approximate curve or the plot of errors, so that a decompressed reconstructed image based on the decompressed reconstructed data can be displayed. While viewing the displayed reconstructed image, the user can select a reconstructed image in which the deterioration quantity is permissible, and the compression ratio corresponding to that deterioration quantity can be selected as the optimum compression ratio.

According to the first embodiment described above, the parameter relating to the compression ratio of raw data is determined based on the error of the reconstructed image after provisional reconstruction, so that the data compression efficiency can be improved, while the deterioration quantity of the reconstructed image is being taken into account.

Second Embodiment

In the first embodiment, it is assumed that a parameter relating to a compression ratio optimum for a run time (inference phase) of the data compression apparatus is determined. The second embodiment is an example in which a trained model obtained through training of a deep convolutional neural network (DCNN) or the like is applied to the compressed data when using the data compression apparatus.

The data compression apparatus of the second embodiment has the same configuration as that shown in the block diagram of the data compression apparatus depicted in FIG. 1. The data compression apparatus 1 of the second embodiment differs from the data compression apparatus 1 of the first embodiment in that a trained model is used in the decompression function 23 or the reconstruction function 24.

A first example of the trained model according to the second embodiment will be explained with reference to FIG. 4.

The trained model is obtained through training of a multilayered network represented by the DCNN, such as a deep neural network, a residual network (ResNet), and DenseNet, using training data.

During a training phase, training data is used, which is obtained by using compressed data as input data, and using, as correct answer data, main reconstructed data obtained through not the provisional reconstruction processing but the main reconstruction processing used on raw data for an actual image diagnosis. The multilayered network training is performed by using the training data, so that the trained model is generated.

Figure 4:
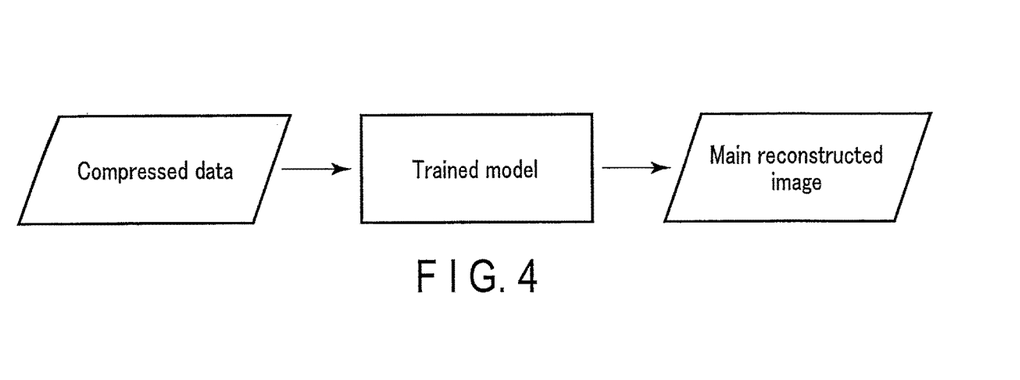
FIG. 4 is a diagram showing a first example of a trained model according to a second embodiment.

During an inference phase, as shown in FIG. 4, by executing the reconstruction function 24, the processing circuitry 2 applies the trained model to the compressed data, thereby generating the main reconstruction image.

Next, a second example of the trained model according to the second embodiment will be explained with reference to FIG. 5.

During a training phase, training data is used, which is obtained by using the compressed data as input data and the raw data before compression processing as correct answer data. The multilayered network training is performed by using the training data, so that the trained model is generated.

Figure 5:
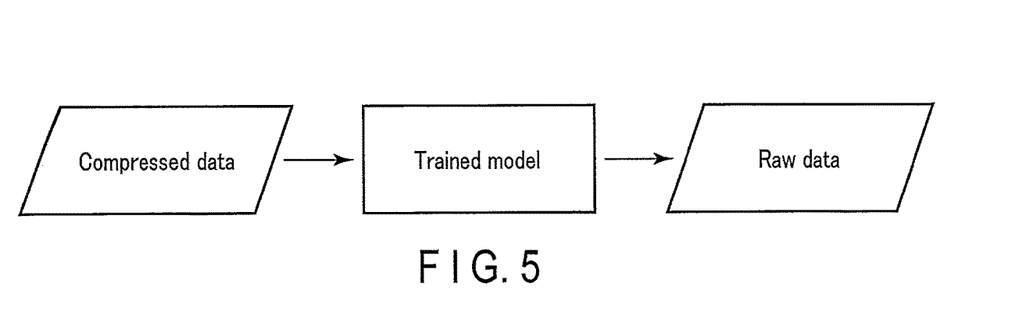
FIG. 5 is a diagram showing a second example of a trained model according to the second embodiment.

During the inference phase, as shown in FIG. 5, by executing the decompression function 23, the processing circuitry 2 applies the trained model to the compressed data, thereby generating raw data before compression processing. Thereafter, the raw data before the compression processing is subjected to the main reconstruction processing, so that the main reconstructed data can be generated.

Figure 6:
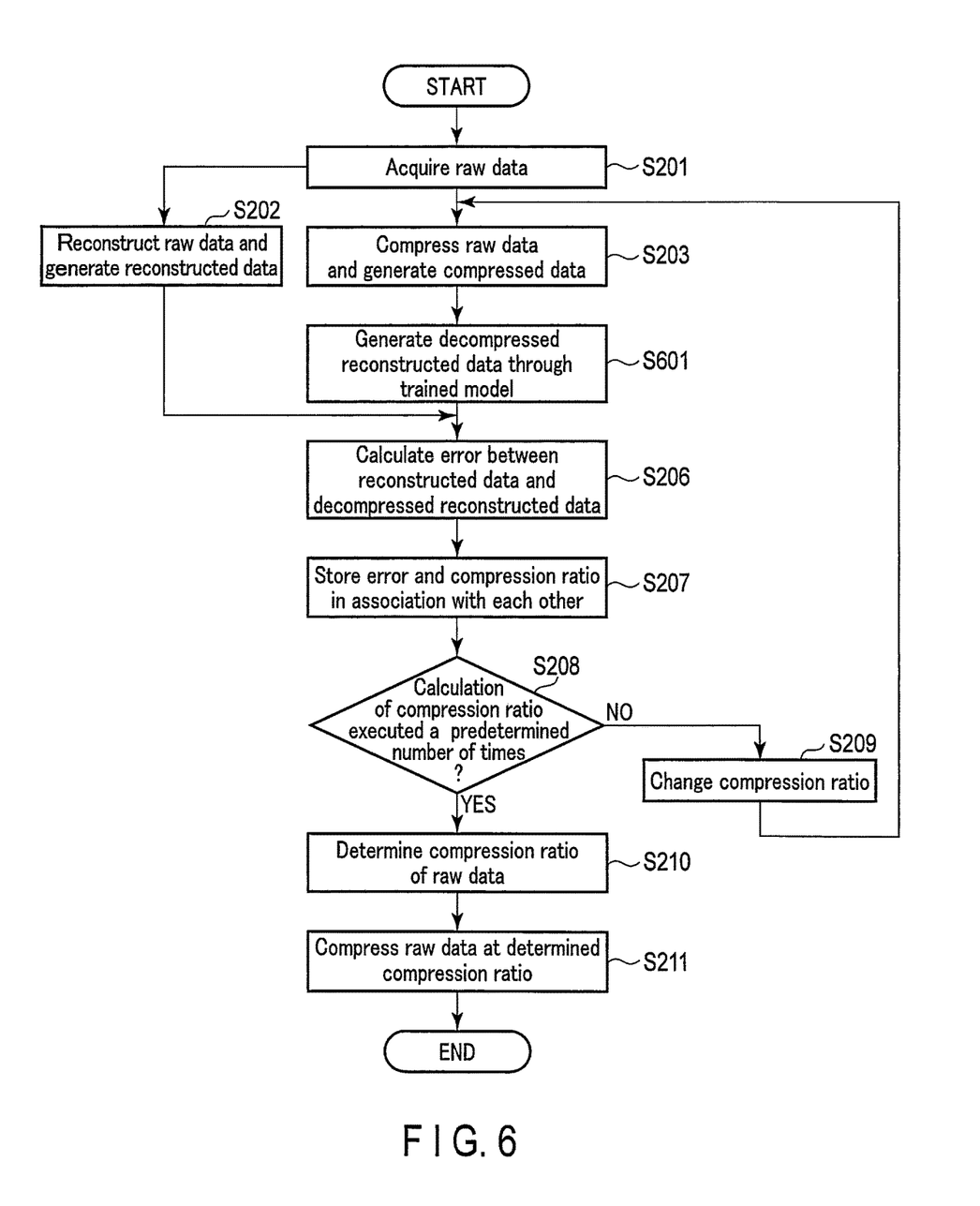
FIG. 6 is a flowchart showing an example of an operation of a data compression apparatus according to the second embodiment.

Next, an operation of the data compression apparatus 1 according to the second embodiment will be described with reference to the flowchart of FIG. 6. The processing in step S201, step S203, and step S206 to step S211 is the same as that in the first embodiment, and explanations thereof will be omitted. Furthermore, it is assumed that the trained model shown in FIG. 4 is used. The reconstruction processing in step S202 is assumed to be the main reconstruction processing (iterative reconstruction) which is the same as that used in the training phase for the trained model.

In step S601, by executing the reconstruction function 24, the processing circuitry 2 applies the trained model to the compressed data, thereby generating decompressed reconstructed data. If the trained model shown in FIG. 5 is used, namely, if the processing circuitry 2 applies the trained model to the compressed data to generate the raw data before the compression processing by executing the decompression function 23, the main reconstruction processing is executed on the raw data generated by applying the trained model to the compressed data, thereby generating the main reconstructed data.

According to the second embodiment described above, the decompressed reconstructed data can be generated from the compressed data in a short period of time at a low cost by applying the trained model. Therefore, in the same manner as in the first embodiment, the data compression efficiency can be improved while accounting for the deterioration quantity of the reconstruction image.

Third Embodiment

In the third embodiment, the processing circuitry of the data compression apparatus 1 functions as a learning apparatus, and the trained model obtained through training is operated as a data compression apparatus.

A training phase of the trained model according to the third embodiment will be explained with reference to FIG. 7.

Figure 7:
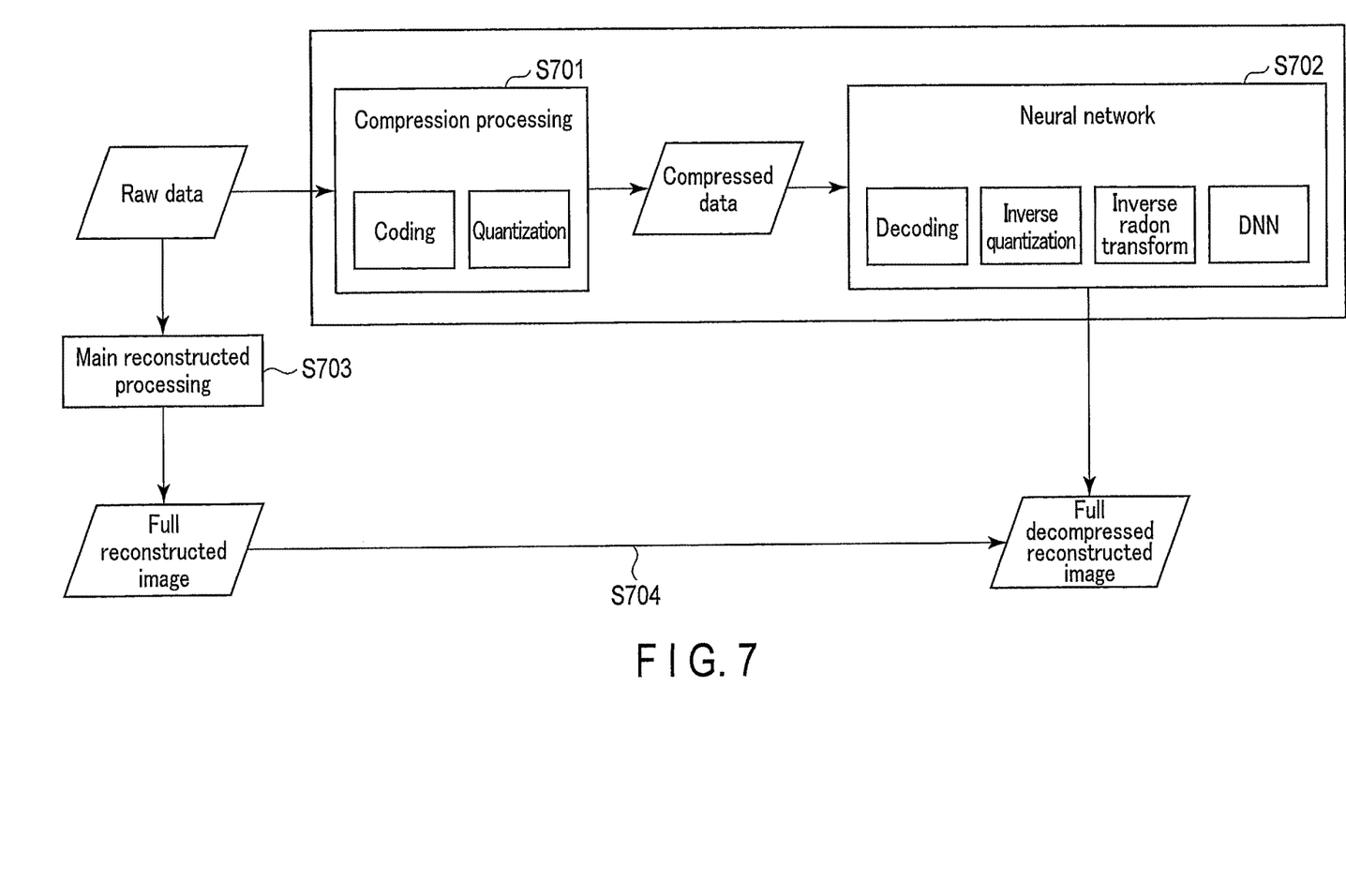
FIG. 7 is a diagram showing a concept of training phase of a data compression apparatus according to a third embodiment.

FIG. 7 is a block diagram showing a flow in the training phase of the data compression apparatus 1.

In the data compression apparatus 1 during the training phase, each of the functions of the processing circuitry 2 operates as a learning apparatus.

The acquisition function 21 acquires raw data.

In step S701, the compression function 22 compresses the raw data, thereby generating compressed data. Specifically, the compression function 22 quantizes and codes the raw data, thereby generating compressed data.

In step S702, the decompression function 23 and the reconstruction function 24 realize processing corresponding to the main reconstruction processing (iterative reconstruction in this embodiment) by applying a neural network. In other words, neural network training is used so as to generate a reconstructed image (hereinafter referred to as a full decompressed reconstructed image) obtained by applying the neural network to the compressed data. The neural network depicted as step S702 includes inverse quantization processing, inverse radon transform processing, and a deep neural network. The iterative reconstruction method may be added to the inverse radon transform.

In step S703, the reconstruction function 24 performs the main reconstruction processing on the raw data, thereby generating a full reconstructed image.

In step S704, the determination function 25 performs training so as to output a compression ratio that may minimize a loss function, which is an error between a full decompressed reconstructed image generated in step S702 and a full reconstructed image generated in step S703. As a result, a coefficient of the neural network used in step S702 is trained, so that a trained model is generated. Therefore, it is possible to realize a data compression apparatus that generates compressed data compressed with the parameter of the optimum compression ratio by applying the trained model to the raw data.

The error between the raw data and the decompressed data obtained in step S703 may be a loss function. For example, a weighting sum of the error between the full reconstructed image and the full decompressed reconstructed image and the error between the raw data and the decompressed data may be estimated as a loss function. Thus, the full reconstructed image can be generated with a limitation that the decompressed data should not greatly deviate from the original raw data.

Furthermore, the magnitude of an absolute value of compressed data may be added to the loss function as a weighting sum. Accordingly, it is possible to add a limitation that the compression ratio can be reduced.

According to the third embodiment described above, a learning apparatus that generates a trained model can be realized by network training to output compressed data obtained by compressing raw data with a parameter relating to a more appropriate compression ratio.

Fourth Embodiment

In the fourth embodiment, the data compression apparatus according to the first embodiment or the second embodiment is applied to a medical image diagnosis apparatus.

A medical image diagnosis system according to the fourth embodiment will be explained with reference to the block diagram of FIG. 8.

Figure 8:
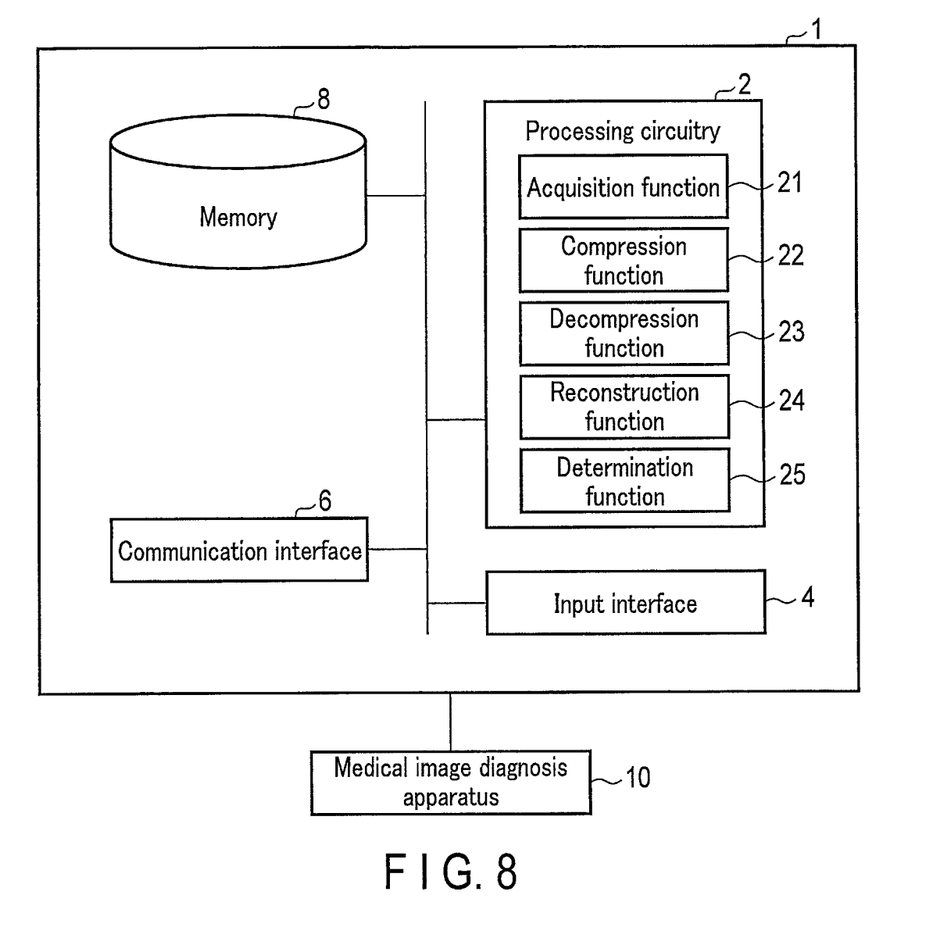
FIG. 8 is a block diagram showing a medical image diagnosis system according to a fourth embodiment.

A medical image diagnosis system shown in FIG. 8 includes a data compression apparatus 1 and a medical image diagnosis apparatus 10.

The medical image diagnosis apparatus 10 is assumed to be, for example, at least one of a CT apparatus, an X-ray imaging apparatus, an MRI apparatus, a positron emission tomography (PET) apparatus, a single photon emission computed tomography (SPECT) apparatus, and an ultrasonic diagnosis apparatus. The medical image diagnosis apparatus 10 acquires medical data as raw data. Specifically, the following medical data is acquired as raw data: detection data or sinogram data if the medical image diagnosis apparatus 10 is a CT apparatus; k-space data, sinogram data, or hybrid space data with only some dimensions Fourier transformed if the apparatus 10 is an MRI apparatus; X-ray imaging data if the apparatus 10 is an X-ray imaging apparatus; PET data if the apparatus 10 is a PET apparatus; SPECT data if the apparatus 10 is a SPECT apparatus; and ultrasonic data if the apparatus 10 is an ultrasonic diagnosis apparatus.

The data compression apparatus 1 acquires raw data from the medical image diagnosis apparatus 10 and compresses the raw data at an optimum compression ratio.

In the example shown in FIG. 8, it is assumed that the raw data is transmitted by data communication from the medical image diagnosis apparatus 10 to the data compression apparatus 1, whereas compressed data is transmitted by data communication from the data compression apparatus 1 to an external apparatus (for example, a work station, a picture archiving and communication system (PACS)), but the embodiment is not limited to this example.

For example, if the medical image diagnosis apparatus 10 is a CT apparatus, the data compression apparatus 1 is mounted on a data acquisition system (DAS), and detection data, namely, raw data acquired by an X-ray detector, may be compressed and transferred to a console.

According to the fourth embodiment described above, raw data acquired by various medical image diagnosis apparatuses are compressed at an optimum compression ratio in consideration of a deterioration quantity of the reconstructed image, so that a large amount of data, such as raw data, can be efficiently compressed.

According to at least one of the embodiments described above, data can be compressed efficiently.

Furthermore, the functions described in connection with the above embodiments may be implemented by, for example, installing a program for executing the processes in a computer, such as a workstation, etc., and expanding the program in a memory. The program that causes the computer to execute the processing can be stored and distributed by means of a storage medium, such as a magnetic disk (a hard disk, etc.), an optical disk (CD-ROM, DVD, Blu-ray (registered trademark) etc.), and a semiconductor memory.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A learning apparatus comprising processing circuitry configured to:
   acquire reconstructed data generated by performing reconstruction processing on data;
   acquire decompressed reconstructed data generated by performing the reconstruction processing on decompressed data obtained by decompressing compressed data that is generated by performing compression processing on the data; and
   generate a trained model, to which data is input and which outputs compressed data, by training a coefficient of a neural network using a loss function, the loss function relating to (1) an error between the reconstructed data and the decompressed reconstructed data and (2) an error between the data and the decompressed data.

* * * * *